United States Patent
Xu et al.

(10) Patent No.: US 7,820,692 B2
(45) Date of Patent: Oct. 26, 2010

(54) TETRAHYDRO ISOQUINOLINE DERIVATIVES, PREPARATION METHODS AND MEDICINAL USES THEREOF

(75) Inventors: Yungen Xu, Nanjing (CN); Jinggen Liu, Shanghai (CN); Ting Guo, Nanjing (CN); Dechuan Wang, Nanjing (CN); Tianjiang Sun, Taizhou (CN); Hongguo Lu, Taizhou (CN)

(73) Assignees: China Pharmaceutical University, Jiangsu (CN); Shanghai Institute of Materia Medica, Chinese Academy of Sciences, Shanghai (CN); Yangtze River Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 12/309,299

(22) PCT Filed: Jul. 10, 2007

(86) PCT No.: PCT/CN2007/002115

§ 371 (c)(1),
(2), (4) Date: Mar. 17, 2009

(87) PCT Pub. No.: WO2008/009215

PCT Pub. Date: Jan. 24, 2008

(65) Prior Publication Data

US 2009/0275607 A1   Nov. 5, 2009

(30) Foreign Application Priority Data

Jul. 12, 2006   (CN) .................. 2006 1 0088349

(51) Int. Cl.
*A61K 31/4725* (2006.01)
*C07D 217/00* (2006.01)
(52) U.S. Cl. ...................... 514/307; 546/146
(58) Field of Classification Search ............. 514/307; 546/146
See application file for complete search history.

(56) References Cited

U.S. PATENT DOCUMENTS

2006/0104907 A1   5/2006   Lazarus et al.

FOREIGN PATENT DOCUMENTS

CN   1887872 A   1/2007
WO   WO 97/31940   9/1997

OTHER PUBLICATIONS

Joel R. Huff, HIV Protease: A Novel Chemotherapeutic Target for AIDS, 1991, Journal of Medicinal Chemistry, vol. 34, No. 8, 2305-2314.*
International Search Report, dated Sep. 6, 2007, correspodning to PCT/CN2007/002115.

* cited by examiner

*Primary Examiner*—Kamal A Saeed
*Assistant Examiner*—Kristin Bianchi
(74) *Attorney, Agent, or Firm*—Christie, Parker & Hale, LLP

(57) ABSTRACT

A kind of tetrahydro isoquinoline derivatives (I), their preparation methods, medicine compositions and medicinal uses thereof, especially their uses as κ-opioid receptor excitant in pain relieving, which belongs to the medicine chemistry. The substituents $R^1$, $R^2$, $R^3$, $R^4$ of general formula (I) are defined as the description.

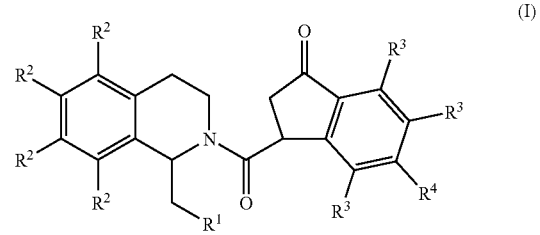

10 Claims, 2 Drawing Sheets

TETRAHYDRO ISOQUINOLINE DERIVATIVES, PREPARATION METHODS AND MEDICINAL USES THEREOF

CROSS-REFERENCE TO RELATED APPLICATION

This application is a National Phase Patent Application and claims the priority of International Application Number PCT/CN2007/002115, filed on Jul. 10, 2007, which claims priority of Chinese Patent Application Number 200610088349.0, filed on Jul. 12, 2006.

TECHNICAL FIELD

The present invention relates to medicine chemistry field, particularly relates to a kind of tetrahydro isoquinoline derivatives and the preparation methods, pharmaceutical compositions and medicinal uses thereof, more particularly relates to the use as κ-opioid receptor agonist in analgesic.

BACKGROUND ART

κ-Receptor, together with μ-, δ-, α-, and ORL-1 receptors, belongs to opioid receptor family. μ-Receptor agonist medicine, represented by morphine, has powerful analgesic efficacy, but has many limits in clinical uses due to its side effects, such as dependence and addiction. The central selective κ-receptor agonist not only can be used for analgesic, but also can avoid morphine-like side effects. It can be used for analgesic, antiphlogistic and analgesic, anti-hyperpathia, treating labor pain; used as aquaretic agents, antipruritic; and used for anticonvulsant treatment, anti-hypertension, neural protection, treating HIV infection, and also used in withdrawal of cocaine and morphine addiction. Therefore, selective κ-receptor agonist medicine has good application prospect.

SUMMARY OF THE INVENTION

The present invention discloses a series of novel tetrahydro isoquinoline derivatives. According to radioligand binding assays, the compound of the invention has very high compatibility and selectivity for κ-receptor. In analgesic test for mice, it shows good analgesic activity.

The general formula I of the compound of the invention is as below:

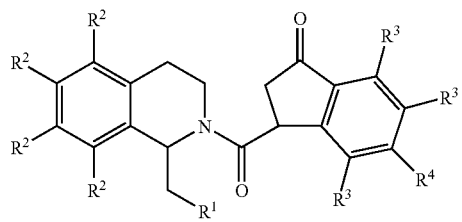

wherein $R^1$ represents:

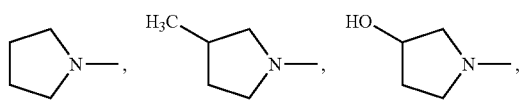

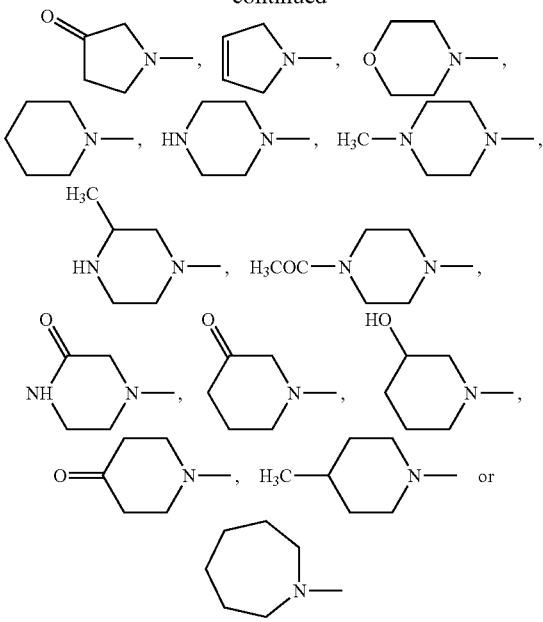

$R^2$ each independently represents: H, F, Cl, Br, $C_1$-$C_4$ alkyl, $OR^5$, or $NR^6R^7$, or form 5,6-methylenedioxy, 6,7-methylenedioxy, or 7,8-methylenedioxy together.

$R^3$ and $R^4$ each independently represent: H, F, Cl, Br, trifluoromethyl, $C_1$-$C_4$ alkyl, $OR^5$, $NR^8R^9$, or form 4,5-methylenedioxy, 5,6-methylenedioxy, or 6,7-methylenedioxy together.

$R^5$ represents: H, $C_1$-$C_4$ alkyl, allyl, $C_3$-$C_7$ cycloalkyl (preferably cyclopropyl, cyclobutyl, or cyclopentyl);

$R^6$ and $R^7$ each independently represent: H, $C_1$-$C_4$ alkyl, $C_1$-$C_4$ alkylacyl (preferably formyl, acetyl, or propionyl), or $C_1$-$C_4$ alkylsulfonyl (preferably methylsulfonyl, or ethylsulfonyl);

$R^8$ and $R^9$ each independently represent: H, $C_1$-$C_4$ alkyl, allyl, $C_1$-$C_4$ alkylacyl (preferably formyl, acetyl, or propionyl), or $C_1$-$C_4$ alkylsulfonyl (preferably methylsulfonyl, or ethylsulfonyl); or form 3-7 membered ring group together with N atom.

Preferably, the compound of general formula I is:

$R^1$ represents

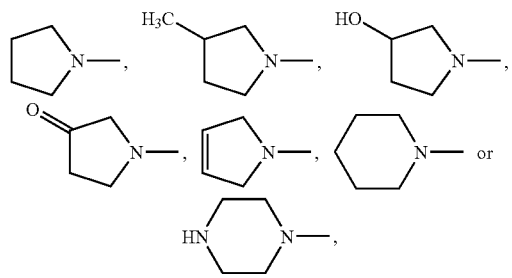

$R^2$ each independently represents: H, F, Cl, methyl, hydrox, methoxy, dimethylamino, or form 5,6-methylenedioxy or 6,7-methylenedioxy group together;

R³ and R⁴ each independently represent: H, F, Cl, methyl, hydroxyl, methoxy, dimethylamino, or form 4,5-methylenedioxy, 5,6-methylenedioxy or 6,7-methylenedioxy together.

More preferably, the compound is:
R¹ represents

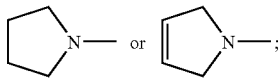

R² each independently represents H, F, Cl or methoxy; R³ and R⁴ represent H, F, Cl, or methoxy.

Most preferably, the compound is
R¹ represents:

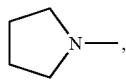

R² represents H, R³ represents H, and R⁴ represents Cl.

According to the present invention, the pharmaceutically acceptable salt comprises acid addition salt formed by the compound of the general formula I and the following acids: hydrochloric acid, hydrobromic acid, sulfuric acid, carbonic acid, citric acid, tartaric acid, phosphoric acid, lactic acid, pyruvic acid, acetic acid, maleic acid, mesylate, benzene sulfonic acid, β-toluene sulphonic acid, or arginine.

Part compounds of the present invention are:
1-(pyrrolidine-1-methyl)-2-(2,3-dihydro-inden-3-keto-1-carbonyl)-1,2,3,4-tetrahydroisoquinoline (I-1)
1-(3-methyl-pyrrolidine-1-methyl)-2-(2,3-dihydro-inden-3-keto-1-carbonyl)-1,2,3,4-tetrahydroisoquinoline (I-2)
1-(3-hydroxy-pyrrolidine-1-methyl)-2-(2,3-dihydro-inden-3-keto-1-carbonyl)-1,2,3,4-tetrahydroisoquinoline (I-3)
1-(3-oxo-pyrrolidine-1-methyl)-2-(2,3-dihydro-inden-3-keto-1-carbonyl)-1,2,3,4-tetrahydroisoquinoline (I-4)
1-(pyrrolidine-1-methyl)-2-(5,6-dimethoxy-2,3-dihydro-inden-3-keto-1-carbonyl)-1,2,3,4-tetrahydroisoquinoline (I-5)
1-(pyrrolidine-1-methyl)-2-(6-chloro-2,3-dihydro-inden-3-keto-1-carbonyl)-1,2,3,4-tetrahydroisoquinoline (I-6)
1-(3-hydroxy-pyrrolidine-1-methyl)-2-(6-chloro-2,3-dihydro-inden-3-keto-1-carbonyl)-1,2,3,4-tetrahydroisoquinoline (I-7)
1-(3-methyl-pyrrolidine-1-methyl)-2-(6-chloro-2,3-dihydro-inden-3-keto-1-carbonyl)-1,2,3,4-tetrahydroisoquinoline (I-8)
1-(3-oxo-pyrrolidine-1-methyl)-2-(6-chloro-2,3-dihydro-inden-3-keto-1-carbonyl)-1,2,3,4-tetrahydroisoquinoline (I-9)
1-(pyrrolidine-1-methyl)-2-(5,6-dichloro-2,3-dihydro-inden-3-keto-1-carbonyl)-1,2,3,4-tetrahydroisoquinoline (I-10)
1-(pyrrolidine-1-methyl)-2-(5-fluoro-2,3-dihydro-inden-3-keto-1-carbonyl)-1,2,3,4-tetrahydroisoquinoline (I-11)
1-(pyrrolidine-1-methyl)-2-(4-chloro-2,3-dihydro-inden-3-keto-1-carbonyl)-1,2,3,4-tetrahydroisoquinoline (I-12)
1-(pyrrolidine-1-methyl)-2-(6-methoxy-2,3-dihydro-inden-3-keto-1-carbonyl)-1,2,3,4-tetrahydroisoquinoline (I-13)
7-methoxy-1-(pyrrolidine-1-methyl)-2-(2,3-dihydro-inden-3-keto-1-carbonyl)-1,2,3,4-tetrahydroisoquinoline (I-14)
7-methoxy-1-(pyrrolidine-1-methyl)-2-(5,6-dimethoxy-2,3-dihydro-inden-3-keto-1-carbonyl)-1,2,3,4-tetrahydroisoquinoline (I-15)
7-methoxy-1-(pyrrolidine-1-methyl)-2-(5,6-dichloro-2,3-dihydro-inden-3-keto-1-carbonyl)-1,2,3,4-tetrahydroisoquinoline (I-16)
7-methoxy-1-(pyrrolidine-1-methyl)-2-(5-fluoro-2,3-dihydro-inden-3-keto-1-carbonyl)-1,2,3,4-tetrahydroisoquinoline (I-17)
7-methoxy-1-(pyrrolidine-1-methyl)-2-(6-chloro-2,3-dihydro-inden-3-keto-1-carbonyl)-1,2,3,4-tetrahydroisoquinoline (I-18)
7-methoxy-1-(pyrrolidine-1-methyl)-2-(6-methoxy-2,3-dihydro-inden-3-keto-1-carbonyl)-1,2,3,4-tetrahydroisoquinoline (I-19)
7-hydroxy-1-(pyrrolidine-1-methyl)-2-(2,3-dihydro-inden-3-keto-1-carbonyl)-1,2,3,4-tetrahydroisoquinoline (I-20)
7-hydroxy-1-(pyrrolidine-1-methyl)-2-(5,6-dimethoxy-2,3-dihydro-inden-3-keto-1-carbonyl)-1,2,3,4-tetrahydroisoquinoline (I-21)
7-hydroxy-1-(pyrrolidine-1-methyl)-2-(5,6-dichloro-2,3-dihydro-inden-3-keto-1-carbonyl)-1,2,3,4-tetrahydroisoquinoline (I-22)
7-hydroxy-1-(pyrrolidine-1-methyl)-2-(5-fluoro-2,3-dihydro-inden-3-keto-1-carbonyl)-1,2,3,4-tetrahydroisoquinoline (I-23)
7-hydroxy-1-(pyrrolidine-1-methyl)-2-(6-chloro-2,3-dihydro-inden-3-keto-1-carbonyl)-1,2,3,4-tetrahydroisoquinoline (I-24)
7-hydroxy-1-(pyrrolidine-1-methyl)-2-(6-methoxy-2,3-dihydro-inden-3-keto-1-carbonyl)-1,2,3,4-tetrahydroisoquinoline (I-25)
6,7-dimethoxy-1-(pyrrolidine-1-methyl)-2-(2,3-dihydro-inden-3-keto-1-carbonyl)-1,2,3,4-tetrahydroisoquinoline (I-26)
6,7-dimethoxy-1-(pyrrolidine-1-methyl)-2-(5,6-dimethoxy-2,3-dihydro-inden-3-keto-1-carbonyl)-1,2,3,4-tetrahydroisoquinoline (I-27)
6,7-dimethoxy-1-(pyrrolidine-1-methyl)-2-(5,6-dichloro-2,3-dihydro-inden-3-keto-1-carbonyl)-1,2,3,4-tetrahydroisoquinoline (I-28)
6,7-dimethoxy-1-(pyrrolidine-1-methyl)-2-(5-fluoro-2,3-dihydro-inden-3-keto-1-carbonyl)-1,2,3,4-tetrahydroisoquinoline (I-29)
6,7-dimethoxy-1-(pyrrolidine-1-methyl)-2-(6-chloro-2,3-dihydro-inden-3-keto-1-carbonyl)-1,2,3,4-tetrahydroisoquinoline (I-30)
6,7-dimethoxy-1-(pyrrolidine-1-methyl)-2-(6-methoxy-2,3-dihydro-1H-inden-3-keto-1-carbonyl)-1,2,3,4-tetrahydroisoquinoline (I-31)

The preparation method for the compound of general formula (I) of present invention is as below:

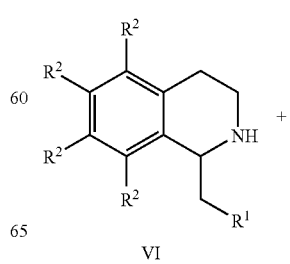

VI

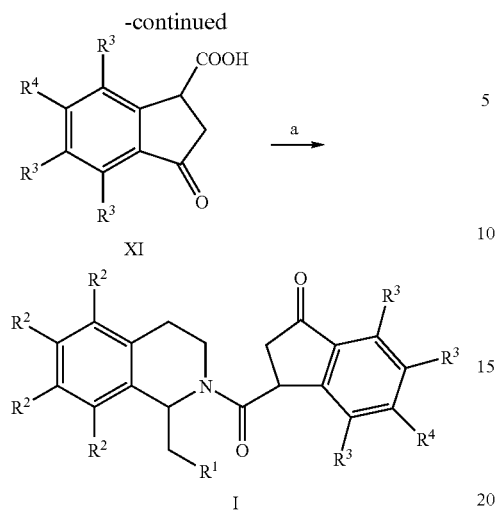

acetonitrile, N,N-dimethylformamide, N,N-dimethylacetamide, or dimethyl sulfoxide) to obtain the compound of general formula (I).

1-(pyrrolidine-1-methyl)-1,2,3,4-tetrahydroisoquinoline series intermediate (VI) is synthesized from (substituted)β-phenylethylamine (general formula II), and the preparation method is as below:

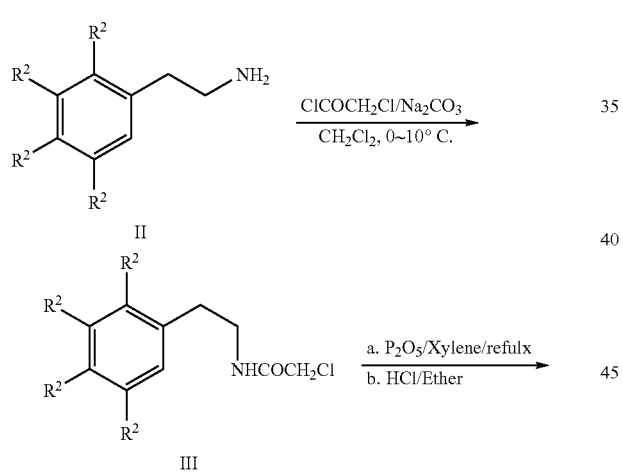

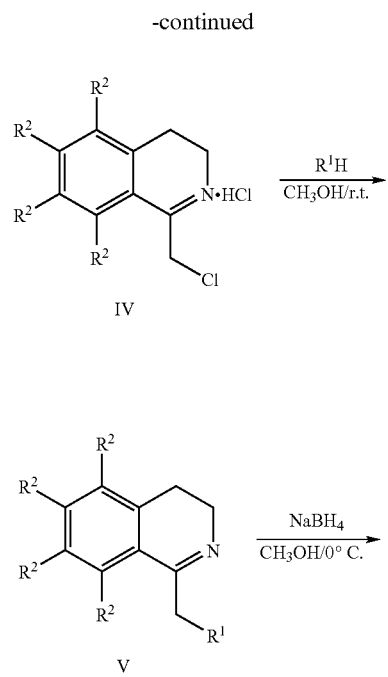

2,3-dihydro-inden-3-keto-1-carboxylic acid series intermediate (XI) is synthesized from (substituted) benzaldehyde (general formula VII), and the preparation method is as below:

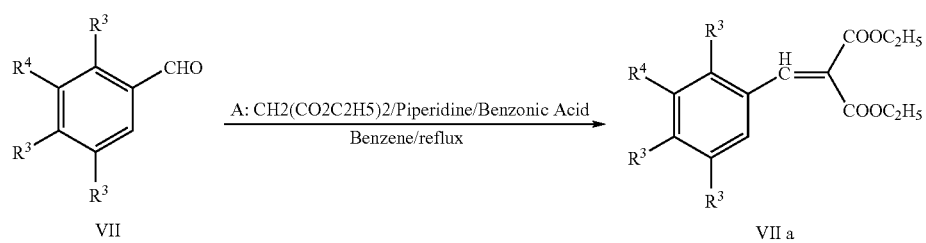

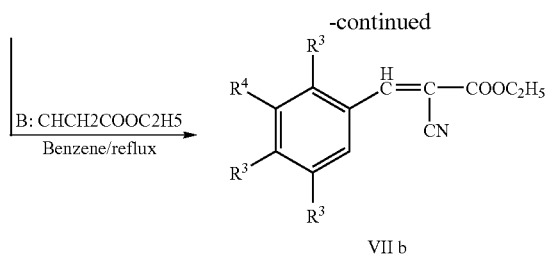

Note: when the raw material is benzaldehyde, route A is adopted; when the raw material is substituted benzaldehyde, route B is adopted.

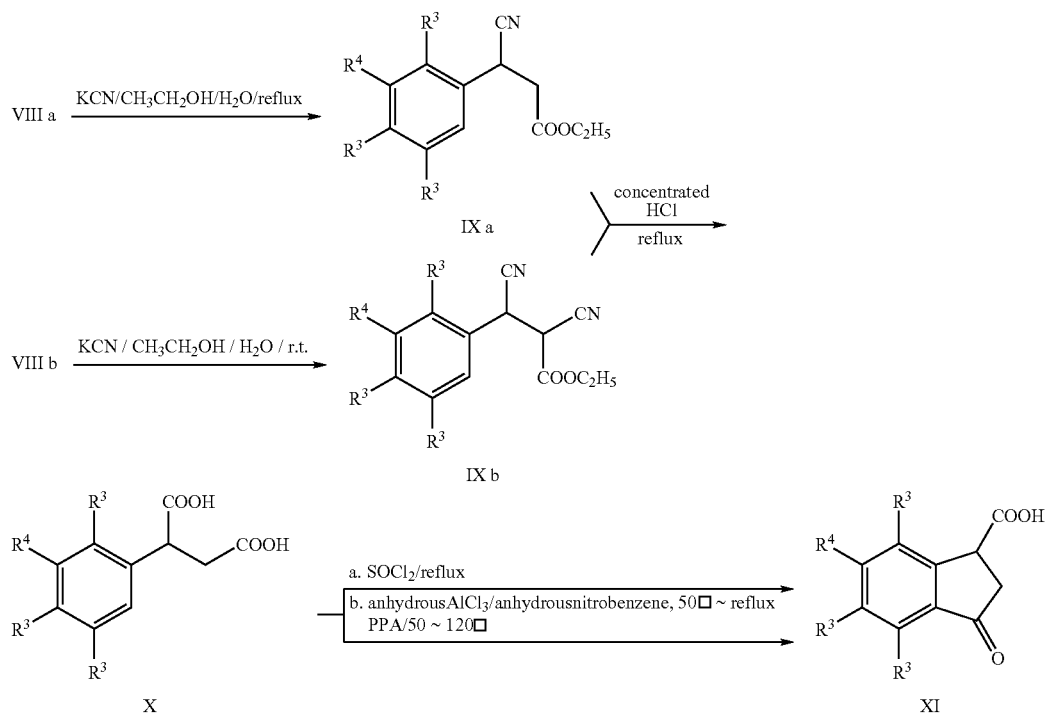

According to the results of radioligand binding assays, the compound of general formula (I) and its pharmaceutically acceptable salt have very high affinity for κ-receptor while having low or extremely low affinity for μ-receptor, and exhibit good selectivity for κ-receptor. In the analgesic ability test which model are mice hot plate method and mice writhing method, it shows good analgesic effect.

The present invention further relates to a pharmaceutical composition for treating diseases relevant to κ-opioid receptor agonist, which contains effective dose of the compound of general formula (I) and pharmaceutically acceptable carrier. The pharmaceutical composition can be in routine preparation forms, such as common tablet or capsule, sustained release tablet or capsule, controlled release tablet or capsule, or injection, etc.

The present invention further relates to the application of the compound of general formula (I) in preparation of medicine for treating or preventing diseases relevant to κ-opioid receptor agonist; wherein the medicine for treating or preventing diseases relevant to κ-opioid receptor agonist is selected from medicines for analgesic, antiphlogistic and analgesic, anti-hyperpathia, and treating labor pain; or medicines for anticonvulsant treatment, anti-hypertension, neural protection, or treating HIV infection; or medicines for withdrawal of cocaine and morphine addiction; or aquaretic agents, antipruritic. Preferably, the disease related to κ-opioid receptor agonist is surgical or cancer pain.

DETAILED DESCRIPTION OF INVENTION

Figure 1:
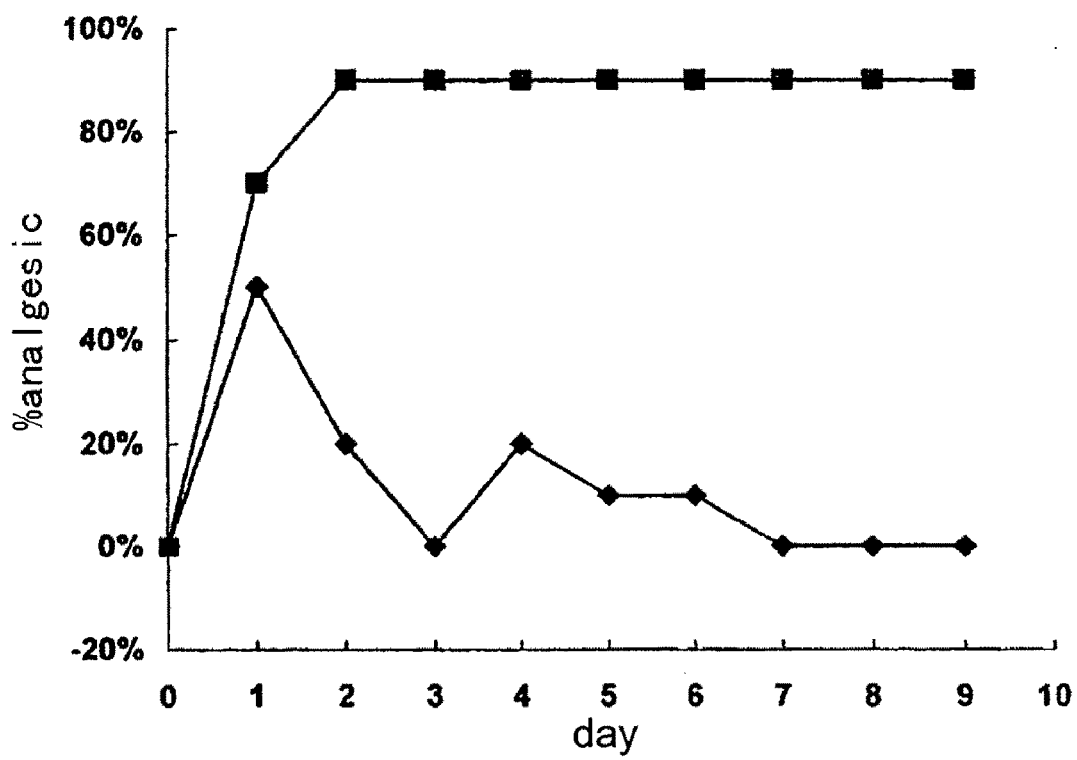
FIG. 1 is the comparison result of tolerance tests for different medicines. The lower rhombic line is morphine, and the upper square line is compound I-6 (25 μg/kg); morphine shows tolerance and efficacy of zero after continuous injection of three days (7 mg/kg), and the dosage is increased to 10 mg/kg on the fourth day.

The preparation embodiments for partial active compounds are as below:

RY-1 type melting point tube; Nicolet Impact 410 IR spectrometer, KBr pellet;

$^1$H-NMR by Bruker AM-500 NMR spectrometer, internal standard TMS; HP1100 Mass spectrograph; Agilent 1100 series LC/MSD Trap SL; Carlo Erba 1106 element analyzer.

Embodiment 1

Preparation of 1-(pyrrolidine-1-methyl)-2-(2,3-dihydro-inden-3-keto-1-carbonyl)-1,2,3,4-tetrahydroisoquinoline (I-1)

Preparation of N-(2-phenylethyl)-2-chloroacetamide (III-1)

Add β-phenylethylamine 36.3 g (0.3 mol), sodium carbonate 31.8 g (0.3 mol), and dichloromethane 300 ml into 500 ml three-necked bottle, control temperature at 0° C. through ice bath, slowly dropwise add chloroacetyl chloride 40.68 g (0.36 mol) within 1 h while stirring, further react at 0° C. for 2 h while stirring to give white turbid solution, slowly add ice water 150 ml, and separate organic layer. Wash the organic layer sequentially with 10% dilute hydrochloric acid solution and saturated salt water, dry with anhydrous sodium sulfate, vacuum evaporate to remove solvent, recrystallize the residue with methanol-water, filter, dry, obtain white needle crystal III-1 36 g, with yield of 61% and mp 61-63° C. (reference value: 60-63° C.).

1-chloromethyl-3,4-dihydro isoquinoline hydrochloride (IV-1)

Add xylene 300 ml and phosphorus pentoxide 28.4 g (0.2 mol) into 500 ml three-necked bottle, increase temperature to 140° C. while mechanical stirring, add compound III-1 9.48 g (0.048 mol) in batch under nitrogen gas protection and immediately the solution turn yellow, react for 3 h under reflux. Cool, and pour out xylene. Slowly add ice water 450 ml into solid residue under ice bath cooling, stir solution for 0.5 h, regulate pH to 11 with 50% NaOH, extract with ethyl ether, and dry with anhydrous sodium sulfate overnight. Filter, introduce dry HCl gas into the filtrate under ice bath, the solution turns from turbid to clear, yellow solid is precipitated on the bottle wall, pour out the solvent and dry it to obtain IV-1 5.3 g, with yield of 51% and mp of 161-163° C. (reference value 163-164° C.).

1-(pyrrolidine-1-methyl)-3,4-dihydroisoquinoline (V-1)

Add methanol 40 ml and tetrahydropyrrole 3.55 g (0.05 mol) under nitrogen gas protection into 100 ml three-necked bottle, control temperature at 0° C. through ice bath, slowly dropwise add methanol solution of compound IV-1 2.66 g (0.0123 mol) while stirring. The temperature of reacting solution is increased to room temperature after dropwise addition, and react overnight to give red transparent solution V-1 which can be directly used for next step of reaction.

1-(pyrrolidine-1-methyl)-1,2,3,4-tetrahydroisoquinoline (VI-1)

controlling temperature at 0° C. through ice bath, add NaBH$_4$ 1.68 g (0.025 mol) in batch into the V-1 solution of the above step, release hydrogen gas and the solution turns to yellow turbid solution. The reacting solution temperature is increased to room temperature after 3 h, evaporate to remove solvent, treat the residue with NaOH and extract it with ethyl ether. Dry the ether layer with anhydrous sodium sulfate overnight. Filter, and evaporate solvent to give orange oil VI-1 crude product 1.46 g, with yield of 55%, which is directly used for next step of reaction.

2-benzyl diethyl malonate (VIII-a)

Add benzaldehyde 21.2 g (0.2 mol), diethyl malonate 32 g (0.2 mol), piperidine 1.2 ml, benzoic acid 0.6 g, and benzene 60 ml into 250 ml eggplant-shaped flask, increase temperature until intensive reflux occurs, use water separator to separate water, and react for 18 h; vacuum evaporate to remove benzene, extract with chloroform-water, wash the organic layer sequentially with water, 1 mol/l hydrochloric acid, and saturated sodium hydrogen carbonate solution, and dry with anhydrous sodium sulfate overnight. Filter, and vacuum evaporate to remove solvent to give orange oil component VIII-a 42.5 g, with yield of 80%, which is directly used for next step of reaction (the pure ester can be obtained by distillation, b.p. 140-142°/4 mm).

β-phenyl-β-cyano ethyl propionate (IX-a)

Add 20 ml aqueous solution of compound VIII-a 50 g (0.2025 mol) and KCN 14 g (0.215 mol), and 500 ml ethanol into 1 L three-necked flask, increase temperature to 65-75° C., react for 18 h while stirring. Cool to 15° C. after reaction, filter to remove KHCO$_3$, wash the filter cake with 20 ml ethanol and combine it with the filtrate. Carefully acidify with diluted hydrochloric acid 5 ml, vacuum concentrate to semi-solid state. Cool, extract with ethyl ether-water, dry the organic layer with anhydrous calcium chloride, filter, and vacuum evaporate to remove solvent to give red oil component IX-a 27 g, with yield of 66%, which is directly used for next step od reaction. (the pure ester can be obtained by distillation, b.p. 161-164°/8 mm).

phenyl butanedioic acid (X-1)

Add compound IX-a 35 g (0.172 mol) and concentrated hydrochloric acid 125 ml into 250 ml eggplant-shaped flask, heat to reflux for 18 h to precipitate orange solid, recrystallize with water, decolore with activated carbon to give pale orange liquid, and freeze to precipitate white solid X-1 27.5 g, with yield of 70%, and m.p. 163-164° (reference value: 163-164°).

2,3-dihydro-inden-3-keto-1-carboxylic acid (XI-1)

Add compound X-1 crude product 3 g (0.017 mol) and SOCl$_2$ 3 ml into 25 ml three-necked flask, mechanically stir, increase temperature to reflux for 0.5 h, slightly cool, add anhydrous nitrobenzene 6 ml and anhydrous AlCl$_3$ 3 g (0.0225 mmol), react at 80° C. for 1.5 h, pour to ice water 75 ml, steam distill to remove all nitrobenzene, add activated carbon 1.5 g for decoloring, hot filter, rapidly shake for cooling to give white water-containing acid with m.p. 84° C. After drying, finally obtain anhydrous acid XI-1 1.2 g, with yield of 61% and m.p. 119-120° C. (reference value 120° C.).

Add compound VI-1 0.97 g (4.5 mmol), compound XI-1 0.95 g (5.4 mmol), DMAP at catalyst quantity, and $CH_2Cl_2$ 20 ml into 50 ml three-necked flask, control temperature at 0° C. through ice bath and stir for 0.5 h, slowly dropwise add DCC 1.3 g (6.3 mmol) dissolved in 10 ml of $CH_2Cl_2$ solution, react overnight under protection of nitrogen gas. React solution turns to orange turbid solution, filter to remove DCU. Subject to column chromatography with petroleum ether:ethyl acetate:triethylamine=4:1:0.1 to give white solid I-1 0.67 g, with yield 40% and mp. 120-122° C.

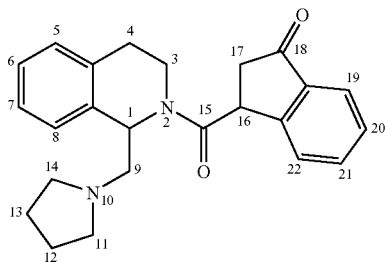

$^1$H-NMR (500 MHz, $CDCl_3$), δ(ppm): 7.74~7.78 (2H, m, $ArH_{19,\underline{19}}$), 7.60 (1H, m, $ArH_{\underline{20}}$), 7.15~7.43 (12H, m, $ArH_{20,21,\underline{21},22,7,\underline{7},8,\underline{8},5,\underline{5},6,\underline{6}}$), 6.99~7.01(1H, d, $H_{22}$), 5.81/5.46~5.49(2H, dd/dd, $H_{1,\underline{1}}$), 4.99~5.01/4.68 (2H, dd/dd, $H_{16,\underline{16}}$), 4.77~4.80/4.27~4.31 (2H, m/m, $H_{3,\underline{3}}$), 3.92~3.98 (1H, m, $H_9$), 3.32~3.37(1H, m, $H_{3'}$), 2.45~3.17 (20H, m, $H_{3',\underline{9},\underline{9'},\underline{9'}}H_{17,\underline{17},17',\underline{17'}}$, $H_{4,\underline{4},4',\underline{4'}}$, $H_{11,\underline{11},11',\underline{11'}}$, $H_{14,\underline{14},14',\underline{14'}}$), 1.67~1.81 (8H, m, $H_{12,\underline{12},12',\underline{12'}}$, $H_{13,\underline{13},13',\underline{13'}}$)

(Note: 1. As the molecule contains two chiral carbons, the product contains two pairs of diastereoisomers, i.e. RR/SS and RS/SR; therefore $^1$H-NMR spectrum shows two groups of hydrogen, this phenomena is also reported in literatures (Charles B K, Willem A L, Joseph P M. Tetrahedron, 2003, 59:8337-8345), and the underscore "_" represents isomers with relatively high content, the same below))

IR ($cm^{-1}$): 3415, 2962, 2929, 2790, 1712 (C=O), 1641 (C=O), 1604, 1434, 1284, 1238, 1043, 761

MS (ESI(+) 70V, m/z): 375.2 ([M+H]$^+$, base peak)

Anal. Calcd. for $C_{24}H_{26}N_2O_2$: C, 76.98; H, 7.00; N, 7.48. Found: C, 76.88; H, 7.07; N, 7.43.

Embodiment 2

1-(pyrrolidine-1-methyl)-2-(5,6-dimethoxy-2,3-dihydro-inden-3-keto-1-carbonyl)-1,2,3,4-tetrahydroisoquinoline (I-5)

α-cyano-β-(3,4-dimethoxyphenyl)-ethyl acrylate (VIII-b-2)

Add 3,4-dimethoxy benzaldehyde 26 g (0.16 mol), ethyl cyanoacetate 18 g (0.16 mol), piperidine 0.8 ml, acetic acid 2.4 g, and benzene 60 ml into 250 ml eggplant-shaped flask, increase temperature to 120-130° C. for intensive reflux, separate water with water separator, react for 12 h. Vacuum evaporate to remove benzene, pour ice water into the reaction solution to precipitate yellow solid, filter and dry to obtain pale yellow crystal VIII-b-2 41 g, with yield almost reaching theoretical value and m.p. 154-156° C. (reference value 156° C.).

α,β-dicyano-β-(3,4-dimethoxyphenyl)-ethyl propionate (IX-b-2)

Add the compound VIII-b-2 52.2 g (0.2 mol), 15 ml of aqueous solution of KCN 14.3 g (0.22 mol), and ethanol 180 ml, reflux react for 40 min while stirring. Cool, carefully add diluted hydrochloric acid for acidification, stir at room temperature overnight. Filter and dry to give white solid. Place the filtrate in refrigerator to precipitate solid again, extract with chloroform-water, and vacuum evaporate to remove chloroform, totally obtain white solid IX-b-2 35 g, with yield of 60% and mp 92-94° C. (reference value 93-95° C.).

3,4-dimethoxy phenyl butanedioic acid (X-2)

The compound IX-b-2 is subjected to the same procedure as preparation of X-1, and refluxed for 8 h under heat; the crude product is recrystallized with water, and decolored with activated carbon to give white solid X-2, with yield of 75% and m.p. 173-174° C. (reference value 172-174° C.).

5,6-dimethoxy-2,3-dihydro-inden-3-keto-1-carboxylic acid (XI-2)

Add PPA 30 g (15 times of the reactant weight) into 25 ml three-necked flask, increase temperature to 70° C. while mechanical stirring, add compound X-2 2 g (8.47 mmol), the color of the reaction system turns from gray to yellow, then to dark red, react at 70° C. for 4 h under nitrogen protection, pour into ice water, extract with chloroform, evaporate to obtain pale yellow solid. Recrystallize with water to give white solid XI-2 1.3 g, with yield of 70% and m.p. 190-190.5° C. (reference value 190-191° C.).

The compound VI-1 and X-2 are subjected to the same procedure as preparation of I-1 to give white solid I-5, with yield of 35% and mp 124-125° C.

$^1$H-NMR (500 MHz, $CDCl_3$), δ(ppm): 6.95~7.27 (10H, m, $ArH_{19,\underline{19},7,\underline{7},8,\underline{8},6,\underline{6},5,\underline{5}}$), 6.30/6.95 (2H, s/s,$_{22,\underline{22}}$), 5.80~5.82/5.51~5.53(2H, dd/dd, $H_{1,\underline{1}}$), 4.85~4.88/4.55~4.57 (2H, dd, $H_{16,\underline{16}}$), 4.82~4.83/4.21~4.25 (2H, m, $H_{3,\underline{3}}$), 3.09, 3.84, 3.91, 3.95 (12H, s, $OCH_3$, $OCH_3$), 3.38~3.48(1H, m, $H_{3'}$), 3.13~3.17(1H, m, $H_9$), 2.45~3.07 (20H, m, $H_{3'}$, $H_{9,\underline{9'},\underline{9'}}$, $H_{17,\underline{17},17',\underline{17'}}$, $H_{4,\underline{4},4',\underline{4'}}$, $H_{11,\underline{11},11',\underline{11'}}$, $H_{14,\underline{14},14',\underline{14'}}$), 1.62~1.81 (8H, m, $H_{12,\underline{12},12',\underline{12'}}$, $H_{13,\underline{13},13',\underline{13'}}$)

IR ($cm^{-1}$): 3493, 2961, 2924, 2805, 2794, 1673 (C=O), 1635 (C=O), 1594, 1503, 1442, 1311 (C—O—C), 1266, 1218, 1191, 1119, 1044 (C—O—C), 854, 771

MS (ESI(+) 70V, m/z): 435.2 ([M+H]$^+$, base peak)

Anal. Calcd. for $C_{26}H_{30}N_2O_4 \cdot H_2O$: C, 69.01; H, 7.13; N, 6.19. Found: C, 68.94; H, 7.08; N, 6.14.

Embodiment 3

1-(pyrrolidine-1-methyl)-2-(6-chloro-2,3-dihydro-inden-3-keto-1-carbonyl)-1,2,3,4-tetrahydroisoquinoline (I-6)

α-cyano-β-(3-chlorophenyl)ethyl acrylate (VIII-b-3)

Use 3-chlorobenzaldehyde as raw material, and perform the same procedures as preparation of VIII-b-2 to give yellow crystal VIII-b-3, with yield almost of theoretic value and mp 100-101° C. (reference value 101° C.).

α-dicyano-β-(3-chlorophenyl)ethyl propionate (IX-b-3)

Add the compound VIII-b-3 53 g (0.225 mol), 16 ml of aqueous solution of KCN 15.5 g (0.237 mol), and ethanol 330 ml, react at room temperature for 18 h while stirring. Carefully add diluted hydrochloric acid for acidification, filter to remove solid insoluble matter, vacuum concentrate, extract with chloroform-water, and vacuum evaporate to remove chloroform to give brown oil matter IX-b-3 36 g, with yield of 62%.

3-chlorophenyl succinic acid (X-3)

The compound IX-b-3 is subjected to the same procedure as preparation of X-1, and refluxed for 8 h under heat; the crude product is recrystallized with ethyl ether-petroleum ether, and decolored with activated carbon to give white solid X-3, with yield of 70% and m.p. 158-160° C. (reference value 161-162° C.).

6-chloro-2,3-dihydro-inden-3-keto-1-carboxylic acid (XI-3)/4-chloro-2,3-dihydro-inden-3-keto-1-carboxylic acid (XI-4)

The compound X-3 is subjected to same procedure as preparation of XI-1 to give carneous solid mixture of XI-3 and XI-4. After column chromatography separation, white solid XI-3 is obtained, with yield of 50% and mp 146-148° C. (reference value: 148-151° C.); white solid XI-4 is also obtained, with yield of 10% and mp 171-174° C. (reference value 171-174° C.).

The compound VI-1 and XI-3 are subjected to the same procedure as preparation of I-1 to give white solid I-6, with yield of 38% and mp 120° C.

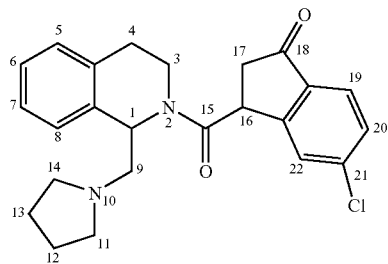

$^1$H-NMR (500 MHz, CDCl$_3$), δ(ppm): 7.66~7.70 (2H, m, ArH$_{20,20'}$), 7.60/6.97 (2H, s/s, ArH$_{22,22'}$), 7.40~7.42/7.31~7.33 (2H, dd/dd, ArH$_{19,19'}$), 7.14~7.29 (8H, d, ArH$_{7,7',8,8',5,5',6,6'}$), 5.80~5.83/5.37~5.39 (2H, dd/dd, H$_{1,1'}$), 4.91~4.93/4.63~4.66(2H, dd/dd, H$_{16,16'}$), 4.74~4.78/4.25~4.28(2H, m/m, H$_{3,3'}$), 3.94~4.00(1H, m, H$_9$), 3.29~3.33/3.22~3.26(2H, m/m, H$_{3',3'}$), 2.44~3.20 (15H, m, H$_{9,9',9''}$, H$_{17,17,17',17'}$, H$_{4,4,4',4'}$, H$_{11,11'}$, H$_{14,14'}$), 2.42~2.45/2.59~2.62(4H, m, H$_{11,11'}$, H$_{14,14'}$), 1.54~1.79 (8H, m, H$_{12,12,12',12'}$, H$_{13,13,13',13'}$)

$^{13}$C-NMR (500 MHz, CDCl$_3$), δ(ppm): 77.2/58.1 (C-1), 55.4 (C-3), 28.6 (C-4), 132.9/126.9 (C-4a), 124.9~129.4 (C-5, C-6, C-7, C-8, C-19, C-20, C-22), 154.9 (C-8a), 61.6/54.8 (C-9), 41.6/40.6 (C-11), 24.0 (C-12), 23.7 (C-13), 40.9 (C-14), 179.9/171.4 (C-15), 40.5/40.4 (C-16), 36.0/29.6 (C-17), 203.9 (C-18), 134.8/134.2 (C-18a), 141.3 (C-21), 135.4/135.2 (C-22a)

IR (cm$^{-1}$): 3471, 3413, 2964, 2929, 2790, 1716 (C=O), 1639 (C=O), 1596, 1440, 825, 744

MS (ESI(+) 70V, m/z): 409.2 ([M+H]$^+$, base peak)

Anal. Calcd. for C$_{24}$H$_{25}$ClN$_2$O$_2$: C, 70.49; H, 6.16; N, 6.85. Found: C, 70.63; H, 6.31; N, 6.74.

The compound I-6 3 g (7.35 mmol) is dissolved in acetone, and dry HCl gas is introduced in ice bath to precipitate white solid I-6.HCl 2.9 g, with yield of 90% and mp 281-282° C.

Anal. Calcd. for C$_{24}$H$_{25}$ClN$_2$O$_2$.HCl.0.5H$_2$O: C, 63.44; H, 5.99; N, 6.16. Found: C, 63.56; H, 6.24; N, 6.09.

Embodiment 4

1-(pyrrolidine-1-methyl)-2-(4-chloro-2,3-dihydro-inden-3-keto-1-carbonyl)-1,2,3,4-tetrahydroisoquinoline (I-12)

The compound VI-1 and the compound XI-4 are subjected to the same procedures as preparation of I-1 to give white solid 1-12, with yield of 40% and mp 135-136° C.

$^1$H-NMR (500 MHz, CDCl$_3$), δ(ppm): 7.14~7.70 (14H, m, ArH), 5.71/5.13~5.15(2H, dd/dd, H$_{1,1'}$), 4.80~4.83/4.53 (2H, dd/dd, H$_{16,16'}$), 4.75~4.79/4.02(2H, m/m, H$_{3,3'}$), 2.44~3.17 (22H, m, H$_{3',3'}$, H$_{9,9',9''}$, H$_{17,17,17',17'}$, H$_{4,4,4',4'}$, H$_{11,11,11',11'}$, H$_{14,14,14',14'}$), 1.54~1.87 (8H, m, H$_{12,12,12',12'}$, H$_{13,13,13',13'}$)

IR (cm$^{-1}$): 3446, 3425, 2956, 2925, 2854, 1724 (C=O), 1618 (C=O), 1460, 1272, 1122, 1068, 821, 779, 754

MS (ESI(+) 70V, m/z): 409.2 ([M+H]$^+$, base peak)

Anal. Calcd. for C$_{24}$H$_{25}$ClN$_2$O$_2$: C, 70.49; H, 6.16; N, 6.85. Found: C, 70.42; H, 6.93; N, 6.56.

Embodiment 5

1-(pyrrolidine-1-methyl)-2-(6-methoxy-2,3-dihydro-inden-3-keto-1-carbonyl)-1,2,3,4-tetrahydroisoquinoline (I-13)

α-cyano-β-(3-methoxyphenyl)ethyl acrylate (VIII-b-4)

Use 3-methoxybenzaldehyde as raw material to carry out the same procedure as preparation of VIII-b-2 to give orange oil matter VIII-b-4, with yield of almost theoretical value, which can be directly used in next step of reaction.

α,β-dicyano-β-(3-methoxyphenyl)ethyl propionate (IX-b-4)

Add the compound VIII-b-4 69.3 g (0.3 mol), 25 ml of aqueous solution of KCN 25.35 g (0.39 mol), and ethanol 480 ml into 500 ml three-necked flask, react at room temperature for 18 h while stirring, carefully add diluted hydrochloric acid for acidification, refrigerate, filter, dry to obtain brown-yellow solid, recrystallize with ethanol-water to obtain white solid IX-b-4 46.44 g, with yield of 60% and mp 73° C.

3-methoxyphenyl succinic acid (X-4)

The compound IX-b-4 is subjected to the same procedure as preparation of X-1, and refluxed for 8 h under heat; the crude product is recrystallized with acetone, and decolored with activated carbon to give white solid X-4, with yield of 78% and m.p. 174-175° C. (reference value 174-175° C.).

6-methoxy-2,3-dihydro-inden-3-keto-1-carboxylic acid (XI-5)

The compound X-4 is subjected to same procedure as preparation of XI-2 to give white solid XI-5 with yield of 75% and mp 186-187.5° C. (reference value: 186-187.5° C.).

The compound VI-1 and XI-5 are subjected to the same procedure as preparation of I-1 to give white solid I-13, with yield of 37% and mp 143-144° C.

$^1$H-NMR (500 MHz, CDCl$_3$), δ(ppm): 7.66~7.67/7.62~7.63(2H, d/d, ArH$_{19,19'}$), 7.12~7.25 (8H, m, ArH$_{20,20',7,7',8,8',5,5'}$), 7.02/6.35(2H, s/s, ArH$_{22,22'}$), 6.94~6.95/6.81~6.83(2H, dd/dd, ArH$_{6,6'}$), 5.78/5.46~5.49(2H, dd/dd, H$_{1,1'}$), 4.89~4.91/4.57 (2H, dd/dd, H$_{16,16'}$), 4.80~4.84/4.20~4.22 (2H, m, H$_{3,3'}$), 3.20, 3.87 (6H, s, OCH$_3$, OCH$_3'$), 3.36~3.40/3.17 (2H, m/m, H$_{3',3'}$), 2.66~3.04 (16H, m, H$_{9,9,9',9'}$, H$_{17,17,17',17'}$, H$_{4,4,4',4'}$, H$_{11,11'}$, H$_{14,14'}$), 2.45~2.59 (4H, m, H$_{11,11'}$, H$_{14,14'}$), 1.60~1.94 (8H, m, H$_{12,12,12',12'}$, H$_{13,13,13',13'}$)

IR (cm$^{-1}$): 3463, 3419, 2931, 2819, 1701 (C=O), 1643 (C=O), 1596, 1433, 1286, 1244 (C—O—C), 1087 (C—O—C), 831, 748

MS (ESI(+) 70V, m/z): 405.1 ([M+H]$^+$, base peak)

Anal. Calcd. for C$_{25}$H$_{28}$N$_2$O$_3$: C, 74.23; H, 6.98; N, 6.93. Found: C, 73.73; H, 7.41; N, 7.35.

Embodiment 6

7-methoxy-1-(pyrrolidine-1-methyl)-2-(2,3-dihydro-inden-3-keto-1-carbonyl)-1,2,3,4-tetrahydroiso-quinoline (I-14)

N-[2-(4-methoxyphenethyl)-ethyl]-2-chloro acetamide (III-2)

Use 4-methoxyphenylethylamine as raw material, and carry out same procedure as preparation of III-1 to give white crystal III-2, with yield of 72% and mp 99-100° C. (reference value 99-100° C.).

1-chloromethyl-7-methoxy-3,4-dihydroisoquinoline hydrochloride (IV-2)

The compound III-2 is subjected to the same procedure as preparation of IV-1 to give yellow solid IV-2, with yield 64% and mp 138-141° C. (reference value 138-141° C.).

1-(pyrrolidine-1-methyl)-7-methoxy-3,4-dihydroisoquinoline (V-2)

The compound IV-2 is subjected to the same procedure as preparation of V-1 to give brown yellow transparent liquid V-2 which is used directly for next step of reaction.

1-(pyrrolidine-1-ylmethyl)-7-methoxy-1,2,3,4-tetrahydroisoquinoline (VI-2)

The compound V-2 is subjected to the same procedure as preparation of VI-1 to give orange oil VI-2 crude product, with yield 60%, which is used directly for next step reaction.

The compound VI-2 and XI-1 are subjected to the same procedures as preparation of I-1 to give white solid I-14, with yield 42% and mp 135-136° C.

$^1$H-NMR (500 MHz, CDCl$_3$), δ(ppm): 7.59~7.77 (4H, m, ArH$_{19,19',20,20'}$), 7.33~7.44, 7.12~7.14 (4H, m, ArH$_{21,21',22,22'}$), 7.05~7.06/7.00~7.02(2H, d/d, ArH$_{5,5'}$), 6.83~6.85, 6.73~6.78 (4H, m, ArH$_{6,6,8,8'}$), 5.79/5.42~5.44 (2H, dd/dd, H$_{1,1'}$), 4.97~5.00/4.74~4.76 (2H, dd/dd, H$_{16,16'}$), 4.77~4.78/4.26~4.30(2H, m/m, H$_{3,3'}$), 3.88~3.94/3.121~3.129 (2H, m, H$_{9,9'}$), 3.78, 3.83 (6H, s, OCH$_3$, OCH$_3'$), 3.32~3.36(1H, m, H$_{3'}$), 2.52~3.01 (19H, m, H$_{3'}$, H$_{9',9'}$, H$_{17,17,17',17'}$, H$_{4,4,4',4'}$, H$_{11,11,11',11'}$, H$_{14,14,14',14'}$), 1.69~1.81 (8H, m, H$_{12,12,12',12'}$, H$_{13,13,13',13'}$)

IR (cm$^{-1}$): 3456, 3417, 2929, 2806, 1714 (C=O), 1639 (C=O), 1610, 1502, 1442, 1249 (C—O—C), 1153, 1037 (C—O—C), 765, 811, 765

MS (ESI(+) 70V, m/z): 405.2 ([M+H]$^+$, base peak)

Anal. Calcd. for C$_{25}$H$_{28}$N$_2$O$_3$: C, 74.23; H, 6.98; N, 6.93. Found: C, 74.13; H, 6.88; N, 6.89.

Embodiment 7

7-methoxy-1-(pyrrolidine-1-methyl)-2-(5,6-dimethoxy-2,3-dihydro-inden-3-keto-1-carbonyl)-1,2,3,4-tetrahydroisoquinoline (I-15)

The compound VI-2 and compound XI-2 are subjected to the same procedure as preparation of I-1 to give white solid I-15, with yield 39% and mp 122-124° C.

$^1$H-NMR (500 MHz, CDCl$_3$), δ(ppm): 7.20/7.15(2H, s/s, ArH$_{19,19'}$), 7.11~7.13/7.03~7.05 (2H, dd/dd, ArH$_{5,5'}$), 6.94/6.33(2H, s/s, ArH$_{22,22'}$), 6.80~6.82(2H, m, ArH$_{6,8}$), 6.763~6.768 (2H, m, ArH$_{6',8'}$), 5.76~5.79/5.46~5.48(2H, dd/dd, H$_{1,1'}$), 4.84~4.86/4.54~4.57 (2H, dd, H$_{16,16'}$), 4.80~4.83/4.21~4.24 (2H, m/m, H$_{3,3'}$), 3.17, 3.78, 3.80, 3.85, 3.93, 3.95 (18H, s, OCH$_3$, OCH$_3'$), 3.38~3.42(1H, m, H$_{3'}$), 2.65~3.14 (17H, m, H$_{3'}$, H$_{9,9,9',9'}$, H$_{17,17,17',17'}$, H$_{4,4,4',4'}$, H$_{11,11'}$, H$_{14,14'}$), 2.44~2.62 (4H, m, H$_{11,11'}$, H$_{14,14'}$), 1.63~1.80 (8H, m, H$_{12,12,12',12'}$, H$_{13,13,13',13'}$)

IR (cm$^{-1}$): 3460, 2960, 2794, 1701 (C=O), 1639 (C=O), 1500, 1440, 1296 (C—O—C), 1253, 1215, 1039 (C—O—C), 856, 819

MS (ESI(+) 70V, m/z): 465.5 ([M+H]$^+$, base peak)

Anal. Calcd. for C$_{27}$H$_{32}$N$_2$O$_5$·½H$_2$O): C, 68.48; H, 7.02; N, 5.92. Found: C, 68.95; H, 7.15, N, 5.46.

Embodiment 8

7-methoxy-1-(pyrrolidine-1-methyl)-2-(6-chloro-2,3-dihydro-inden-3-keto-1-carbonyl)-1,2,3,4-tetrahydroisoquinoline (I-18)

The compound VI-2 and XI-3 are subjected to the same procedure as preparation of I-1 to give white solid I-18, with yield 40% and mp 151-153° C.

$^1$H-NMR (500 MHz, CDCl$_3$), δ(ppm): 7.65~7.69 (2H, d/d, ArH$_{20,20'}$), 7.58/6.99 (2H, s/s, ArH$_{22,22'}$), 7.39~7.40/7.30~7.32 (2H, dd/dd, ArH$_{19,19'}$), 7.12~7.14/7.03~7.04(2H, dd, ArH$_{5,5'}$), 6.83~6.86, 6.74~6.77 (4H, m, ArH$_{6,6,8,8'}$), 5.76/5.31~5.32 (2H, dd/dd, H$_{1,1'}$), 4.89/4.62(2H, dd/dd, H$_{16,16'}$), 4.69~4.73/4.21~4.24(2H, m/m, H$_{3,3'}$), 3.90~3.96 (1H, m, H$_{9'}$), 3.78, 3.82 (6H, s, OCH$_3$, OCH$_3'$), 3.28~3.32 (1H, m, H$_{3'}$), 2.65~3.03 (16H, m, H$_{3'}$, H$_{9,9',9'}$, H$_{17,17,17',17'}$, H$_{4,4,4',4'}$, H$_{11,11'}$, H$_{14,14'}$), 2.46~2.59 (4H, m, H$_{11,11'}$, H$_{14,14'}$), 1.64~1.77 (8H, m, H$_{12,12,12',12'}$, H$_{13,13,13',13'}$)

IR (cm$^{-1}$): 3469, 3411, 2956, 2794, 1708 (C=O), 1641 (C=O), 1600, 1436, 1311 (C—O—C), 1242, 1161, 1035 (C—O—C), 881, 835, 806

MS (ESI(+) 70V, m/z): 439.2 ([M+H]$^+$, base peak)

Anal. Calcd. for C$_{25}$H$_{27}$ClN$_2$O$_3$: C, 68.41; H, 6.20; N, 6.38. Found: C, 68.08; H, 6.32; N, 6.11.

Embodiment 9

7-methoxy-1-(pyrrolidine-1-methyl)-2-(6-methoxy-2,3-dihydro-inden-3-keto-1-carbonyl)-1,2,3,4-tetrahydroisoquinoline (I-19)

The compound VI-2 and the compound XI-5 are subjected to the same procedure as preparation of I-1 to give white solid I-19, with yield 34% and mp 144-145° C.

$^1$H-NMR (500 MHz, CDCl$_3$), δ(ppm): 7.71~7.72/7.63~7.64(2H, d/d, ArH$_{19,19'}$), 7.12,7.13 (1H, d/d, ArH$_5$), 7.03~7.05 (2H, m, ArH$_{5',22'}$), 6.94~6.96 (1H, dd/dd, ArH$_{20}$), 6.76~6.84/6.82~6.84(5H, m, ArH$_{20,6,6,8,8}$), 6.36~6.37(1H, s, ArH$_{22}$), 5.75~5.78/5.43~5.45(2H, dd/dd, H$_{1,1}$), 4.88~4.90/4.58~4.60 (2H, dd/dd, H$_{16,16}$) 4.80~4.83/4.21~4.25 (2H, m/m, H$_{3,3}$), 3.24, 3.78, 3.81, 3.87, (12H, s, OCH$_3$, OCH$_3$), 3.37~3.42(1H, m, H$_{3'}$), 2.64~3.17 (17H, m, H$_{3'}$, H$_{9,9,9',9'}$,H$_{17,17,17',17'}$, H$_{4,4,4',4'}$, H$_{11,11'}$, H$_{14,14'}$), 2.45~2.59 (4H, m, H$_{11,11'}$, H$_{14,14'}$), 1.60~1.80 (8H, m, H$_{12,12,12',12'}$, H$_{13,13,13',13'}$)

IR (cm$^{-1}$): 3475, 3415, 2960, 2921, 2804, 1704 (C=O), 1645 (C=O), 1598, 1498, 1436, 1284, 1249 (C—O—C), 1037 (C—O—C), 827, 775

MS (ESI(+) 70V, m/z): 435.2 ([M+H]$^+$, base peak)

Anal. Calcd. for C$_{26}$H$_{30}$N$_2$O$_4$·½H$_2$O): C, 70.41; H, 7.04; N, 6.32. Found: C, 70.71; H, 7.04; N, 6.62.

Embodiment 10

6,7-dimethoxy-1-(pyrrolidine-1-methyl)-2-(2,3-dihydro-inden-3-keto-1-carbonyl)-1,2,3,4-tetrahydroisoquinoline (I-26)

N-[2-(3,4-dimethoxyphenethyl)-ethyl]-2-chloro acetamide (III-3)

3,4-dimethoxyphenylethylamine is adopted as raw material and subjected to the same procedure as preparation of III-1 to give white crystal III-3, with yield 62% and mp 94-95° C. (reference value 94-95° C.).

1-chloromethyl-6,7-dimethoxy-3,4-dihydroisoquinoline hydrochloride (IV-3)

The compound III-3 is subjected to the same procedure as preparation of IV-1 to give yellow solid IV-3, with yield 57% and mp 194-196° C. (reference value 196° C.).

1-(pyrrolidine-1-methyl)-6,7-dimethoxy-3,4-dihydroisoquinoline (V-3)

The compound IV-3 is subjected to the same procedure as preparation of V-1 to give brown yellow transparent liquid V-3 which is used directly for next step reaction.

1-(pyrrolidine-1-methyl)-6,7-dimethoxy-1,2,3,4-tetrahydroisoquinoline (VI-3)

The compound V-3 is subjected to the same procedure as preparation of VI-1 to give orange oil VI-3 crude product, with yield 55%, which is used directly for next step reaction.

The compound VI-3 and XI-1 are subjected to the same procedures as preparation of I-1 to give white solid I-26, with yield 42% and mp 174-175° C.

$^1$H-NMR (500 MHz, CDCl$_3$), δ(ppm): 7.74~7.78 (2H, m, ArH$_{19,20}$), 7.58/7.61 (2H, m, ArH$_{19,20}$), 7.34~7.45(3H, m, ArH$_{21,21,22}$), 7.00,7.01(1H, d/d, H$_{22}$), 6.74, 6.70(2H, s/s, ArH$_{8,8}$), 6.68~6.70, 6.61(2H, s/s, ArH$_{5,5}$), 5.71/5.37~5.40(2H, dd/dd, H$_{1,1}$), 4.96~4.99/4.66 (2H, dd/dd, H$_{16,16}$), 4.78~4.82/4.27~4.31 (2H, m/m, H$_{3,3}$), 3.85, 3.90 (12H, s, OCH$_3$, OCH$_3$), 3.34~3.38(1H, m, H$_{3'}$), 2.66~3.14 (17H, m, H$_{3'}$, H$_{9,9,9',9'}$, H$_{17,17,17',17'}$, H$_{4,4,4',4'}$, H$_{11,11'}$, H$_{14,14'}$), 2.47~2.56 (4H, m, H$_{11,11'}$, H$_{14,14'}$), 1.65~1.78 (8H, m, H$_{12,12,12',12'}$, H$_{13,13,13',13'}$)

IR (cm$^{-1}$): 3448, 3406, 2958, 2790, 1708 (C=O), 1639 (C=O), 1515, 1436, 1257, 1234 (C—O—C), 1120, 1024 (C—O—C), 883, 837, 775

MS (ESI(+) 70V, m/z): 435.5 ([14+H]$^+$, base peak)

Anal. Calcd for C$_{26}$H$_{30}$N$_2$O$_4$: C, 71.87; H, 6.96; N, 6.45. Found: C, 72.19; H, 6.87; N, 6.38.

Embodiment 11

6,7-dimethoxy-1-(pyrrolidine-1-methyl)-2-(5,6-dimethoxy-2,3-dihydro-inden-3-keto-1-carbonyl)-1,2,3,4-tetrahydroisoquinoline (I-27)

The compound VI-3 and the compound XI-2 are subjected to the same procedure as preparation of I-1 to give white solid I-27, with yield 33% and mp 125° C.

$^1$H-NMR (500 MHz, CDCl$_3$), δ(ppm): 7.19/7.15(2H, s/s, ArH$_{19,19}$), 6.94/6.75(2H, s/s, ArH$_{22,22}$), 6.73/6.67(2H, s/s, ArH$_{8,8}$), 6.59/6.36(2H, s/s, ArH$_{5,5}$), 5.70~5.73/5.40~5.43(2H, dd/dd, H$_{1,1}$), 4.84~4.85,4.54~4.56 (2H, dd, H$_{16,16}$), 4.81~4.83, 4.20~4.25 (2H, m/m, H$_{3,3}$), 3.20, 3.85~3.95 (24H, s, OCH$_3$, OCH$_3$), 3.37~3.42(1H, m, H$_{3'}$), 2.65~3.13 (17H, m, H$_{3'}$, H$_{9,9,9',9'}$, H$_{17,17,17',17'}$, H$_{4,4,4',4'}$, H$_{11,11'}$, H$_{14,14'}$), 2.47~2.59 (4H, m, H$_{11,11'}$, H$_{14,14'}$), 1.58~1.80 (8H, m, H$_{12,12,12',12'}$, H$_{13,13,13',13'}$)

IR (cm$^{-1}$): 3415, 2947, 2800, 1695 (C=O), 1633 (C=O), 1500, 1442, 1307

(C—O—C), 1269, 1251, 1215, 1116, 1043 (C—O—C), 864, 775

MS (ESI(+) 70V, m/z): 495.5 ([M+H]$^+$, base peak)

Anal. Calcd. for C$_{28}$H$_{34}$N$_2$O$_6$·H$_2$O: C, 65.61; H, 7.08; N, 5.47. Found: C, 65.79; H, 6.86; N, 5.23.

Embodiment 12

6,7-dimethoxy-1-(pyrrolidine-1-methyl)-2-(6-chloro-2,3-dihydro-inden-3-keto-1-carbonyl)-1,2,3,4-tetrahydroisoquinoline (I-30)

The compound VI-3 and the compound XI-3 are subjected to the same procedure as preparation of I-1 to give white solid I-30, with yield 35% and mp 178-179° C.

$^1$H-NMR (500 MHz, CDCl$_3$), δ(ppm): 7.66~7.70 (2H, d/d, ArH$_{20,20}$), 7.59/7.00 (2H, s/s, ArH$_{22,22}$), 7.40~7.42/7.32~7.33 (2H, dd/dd, ArH$_{19,19}$), 6.69, 6.61(4H, s/s, ArH$_{5,8,8,5}$), 5.72/5.28~5.31 (2H, dd/dd, H$_{1,1}$), 4.90~4.92/4.64(2H, dd/dd, H$_{16,16}$), 4.73~4.77/4.24~4.28(2H, m/m, H$_{3,3}$), 3.86, 3.90 (12H, s, OCH$_3$, OCH$_3$), 3.30~3.34 (1H, m, H$_{3'}$), 2.65~3.03 (17H, m, H$_{3'}$, H$_{9,9,9',9'}$, H$_{17,17,17',17'}$, H$_{4,4,4',4'}$, H$_{11,11'}$, H$_{14,14'}$), 2.46~2.59(4H, m, H$_{11,11'}$, H$_{14,14'}$), 1.64~1.79 (8H, m, H$_{12,12,12',12'}$, H$_{13,13,13',13'}$)

IR (cm$^{-1}$): 3456, 3413, 3328, 2927, 2796, 1712 (C=O), 1637 (C=O), 1591, 1517, 1438, 1313 (C—O—C), 1261, 1238, 1118 (C—O—C), 887, 840, 777

MS (ESI(+) 70V, m/z): 469.2 ([M+H]$^+$, base peak)

Anal. Calcd. for C$_{26}$H$_{29}$ClN$_2$O$_4$: C, 66.59; H, 6.23; N, 5.97. Found: C, 66.48; H, 6.67; N, 5.93.

Embodiment 13

6,7-dimethoxy-1-(pyrrolidine-1-methyl)-2-(6-methoxy-2,3-dihydro-inden-3-keto-1-carbonyl)-1,2,3,4-tetrahydroisoquinoline (I-31)

The compound VI-3 and the compound XI-5 are subjected to the same procedure as preparation of I-1 to give white solid I-31, with yield 44% and mp 193-195° C.

$^1$H-NMR (500 MHz, CDCl$_3$), δ(ppm): 7.70~7.72/7.63~7.64(2H, d/d, ArH$_{19,19}$), 7.02~7.03/6.38~6.39(2H, m/m, ArH$_{22,22}$), 6.94~6.96/6.82~6.84(2H, dd/dd, ArH$_{20,20}$), 6.73/6.67(2H, s/s, ArH$_{8,8}$), 6.67/6.60 (2H, s/s, ArH$_{5,5}$), 5.69~5.72/5.37~5.40(2H, dd/dd, $H_{1,1'}$), 4.87~4.90/4.57~4.60 (2H, dd/dd, $H_{16,16'}$), 4.81~4.84/4.22~4.26 (2H, m/m, $H_{3,3'}$), 3.28, 3.85~3.88 (18H, s, $OCH_3$, $OCH_3$), 3.36~3.41(1H, m, $H_3'$), 2.64~3.13 (17$H_3'$, $H_{9,9',9'}$, $H_{17,17',17'}$, $H_{4,4',4'}$, $H_{11,11'}$, $H_{14,14'}$), 2.46~2.58 (4H, m, $H_{11,11'}$, $H_{14,14'}$), 1.61~1.79 (8H, m, $H_{12,12',12'}$, $H_{13,13',13'}$)

IR ($cm^{-1}$): 3446, 2960, 2933, 2796, 1701 (C=O), 1637 (C=O), 1596, 1515, 1442, 1282, 1253 (C—O—C), 1114, 1022 (C—O—C), 837, 775

MS (ESI(+) 70V, m/z): 465.2 ([M+H]$^+$, base peak)

Anal. Calcd. for $C_{27}H_{32}N_2O_5$: C, 69.81; H, 6.94; N, 6.03. Found: C, 70.04; H, 6.96; N, 5.90.

Experiment Embodiment

Experiment Embodiment 1: Radioligand Receptor Binding Assay

The experiment test tubes are divided into total binding tubes and non-specific binding tubes, and several groups of sample tubes added with competitive ligand in different concentrations are provided. The total binding tube is added with expressed membrane receptor protein equivalent to 20 μg and [$^3$H] diprenorphine (0.5 nM) (1.44 Pbq/mol broad spectrum opioid antagonist, Amersham), the corresponding non-specific binding tubes are further added with 1 μM Naloxone (broad spectrum opioid antagonist, Sigma), the sample tubes are added with different concentrations compounds which are to be screened, the final volume is regulated to 100 μl with 50 mM Tris(Amresco)-HCl (pH 7.4). Incubation is performed at 30° C. for 30 min, and the tubes are placed into ice water to stop reaction. Negative pressure filter is performed in Millipore sample collector via GF/(Whatman) glass fiber filter paper. Ice cold 50 mM Tris-HCl (pH 7.4) is used to wash the filter paper for three times, each for 4 ml; Dry the filter paper and place it in 0.5 ml Eppendorff tube, and add 0.5 ml of lipophilic scintillator liquid (Reagent No. 1 Factory Of Shanghai Chemical Reagent Co. Ltd). Beckman LS 6500 multifunctional liquid scintillation counter is adopted for measuring radiation intensity, calculating inhibition rate is calculated, each concentration has three duplicated tubes, and each tube is independently tested for 3-4 times.

Calculation Method:

$IC_{50}$ value is calculated by software Prism 4.0.

$K_i = IC_{50}/(1+[L]/K_d)$, ([L] is the concentration of added marked ligand, and $K_d$ is equilibrium dissociation constant of radioligand).

Pharmacological test results of partial compounds are as below:

TABLE 1 competition binding experiment data of the partial compounds of the invention with κ-receptor

| | dpm | inhibition rate %$^a$ | | dpm | inhibition rate %$^a$ |
|---|---|---|---|---|---|
| total binding | 3353.96 | | total binding | 3654.03 | |
| non specific binding | 273.74 | | non specific binding | 243.59 | |
| I-1 | 212.91 | 100 | I-5 | 260.58 | 99.5 |
| I-14 | 972.69 | 77.3 | I-6 | 201.00 | 100 |
| I-15 | 820.16 | 82.3 | I-13 | 211.54 | 100 |
| I-18 | 281.00 | 100 | I-26 | 1883.77 | 51.9 |
| I-19 | 799.91 | 82.9 | I-30 | 2269.71 | 40.6 |
| I-27 | 5257.44 | 0 | I-31 | 3271.85 | 11.2 |

$^a$represents inhibition rate of the compound at $1 \times 10^{-5}$ M.

TABLE 2

Affinity (Ki) and competition binding ($IC_{50}$) value of the partial compound of the present invention to κ-opioid receptor

| Compd. | $IC_{50}$ (M) κ | Ki (M) κ |
|---|---|---|
| I-1 | $1.53 \times 10^{-9}$ | $4.38 \times 10^{-10}$ |
| I-5 | $4.69 \times 10^{-9}$ | $1.34 \times 10^{-9}$ |
| I-6 | $1.05 \times 10^{-10}$ | $2.99 \times 10^{-11}$ |
| I-13 | $3.18 \times 10^{-9}$ | $9.09 \times 10^{-10}$ |
| I-14 | $9.12 \times 10^{-7}$ | $2.70 \times 10^{-7}$ |
| I-18 | $5.99 \times 10^{-8}$ | $1.71 \times 10^{-8}$ |

TABLE 3

Affinity (Ki) and competition binding ($IC_{50}$) value of the partial compound of the present invention to μ-opioid receptor, and receptor selectivity μKi/κKi value.

| Compd. | $IC_{50}$ (M) μ | Ki (M) μ | μKi/κKi |
|---|---|---|---|
| I-1 | 18.7% ($^{-6}$)$^a$ | / | / |
| I-5 | $3.18 \times 10^{-7}$ | $1.06 \times 10^{-7}$ | 79 |
| I-6 | $2.00 \times 10^{-6}$ | $6.68 \times 10^{-7}$ | 22341 |
| I-13 | $3.99 \times 10^{-7}$ | $1.33 \times 10^{-7}$ | 146 |
| I-14 | 14.6% ($^{-6}$)$^a$ | / | / |
| I-15 | 11.7% ($^{-6}$)$^a$ | / | / |
| I-18 | 14.0% ($^{-6}$)$^a$ | / | / |

$^a$represents inhibition rate of medicine at $1 \times 10^{-6}$ M.

Experiment Embodiment 2: Mice Hot-Plate Method and Mice Writhing Method for Analgesic Test Analgesic efficacy of the subject compound is determined by using model derived from mice hot plate method and mice writhing method (Methodology of Pharmacological Experiment, edition II, Xu Shuyun, People Medical Publishing Company, 1991).

Mice Hot Plate Method:

1. Material

Experiment Animal: Kuming Mice (Female, 18-22 g)

2. Procedure (1) Selection of normal mice: the test room temperature is controlled at about 22° C., temperature of the hot plate of an pain threshold dector is regulated to 55° C., the duration from the moment the mice is put on the hot plate to the moment the mice start to lick the hind paw is recorded as pain threshold value, the test is repeated twice at interval of 20 min, and the mice with average pain threshold value no more than 30 sec is qualified mice.

(2) Experimental mice: the qualified mice are randomly divided into groups each having 10 mice, and subjected to subcutaneous injection.

Each group is tested for mice pain response time once every 5, 15, 30, 50, and 60 minute after administration, and the medicine is believed to be effective which response time beyond 1 min.

Mice Writhing Assay

I-6 is administered via subcutaneous injection, then 0.6% acetic acid solution (10 ml/kg) is administered after 30 min, and the number of the mice writhing within 15 min is recorded.

3. Experiment Result:

Compared with morphine, compound I-1 and I-6 have powerful analgesic efficacy, and their analgesic activities for mice hot plate method and mice writhing method are shown in Table 4.

TABLE 4

Analgesic experiment result of compound I-1 and compound I-6

|  | Mice hot plate method | Mice writhing assay |
| --- | --- | --- |
| I-1 | 44.147(25.134-77.545) ug/kg | 26.303(16.807-41.165) ug/kg |
| I-6 | 25.000(18.675-33.467) ug/kg | 3.313(1.775-6.183) ug/kg |
| Morphine | 6.949(5.682-8.500) mg/kg | 0.840(0.558-1.265) mg/kg |

Experiment Embodiment 3: Acute Toxicity Test of Compound I-6

1. Procedure

Acute toxicity of compound I-6 is determined according to Methodology of Pharmacological Experiment, edition II, Xu Shuyun (People's Medical Publishing House, 1991), and An Introduction of the Assessment for Novel Drugs, edition II, Qin Boyi (People's Medical Publishing House, 1999).

Kunming mice (body weight 18-22 g, female 6 weeks old, male 4-5 weeks) are provided, randomly divided into groups each having 20 mice (half female, half male). The mice are subjected to adaptive feeding for 1-2 days before administration. Compound I-6 is administered peritoneally for 4 dosage groups, 60 mg/kg, 50 mg/kg, 40 mg/kg, and 30 mg/kg. The mice are normally fed after administration, their conditions, such as drinking, feeding, excreting, activity, and hair color, are observed everyday, their body weights are weighed every other day, and the observation lasts for two weeks.

2. Experiment Result:

The experiment result shows that peritoneal administration at 30 mg/kg has no influence on drinking, feeding, excreting, activities, and hair color of mice. The $LD_{50}$ value of the compound I-6 is 40.147 (36.805-43.792) mg/kg.

Experiment Embodiment 4: Analgesic Tolerance Test of Compound I-6

1. Procedure:

Kuming mice (18-20 g, male) are selected for test, and divided into physiological saline group, morphine group, and I-6 group.

Administration Method:

physiological saline group: subcutaneous administration, 0.2 mL for each mice.

Morphine group: Day 1-3, subcutaneous injection, 7 mg/kg

Day 4-7, subcutaneous injection, 10 mg/kg

Day 8-9, subcutaneous injection, 15 mg/kg

I-6 group: Day 1-9, subcutaneous injection, 25 µg/kg

Hot plate method in mice is adopted as model, administration lasts for 9 days, analgesic effects before and after administration are determined every day, and if analgesic effect is attenuated after continuous administration of 3 days, the drug concentration will be increased, and if analgesic effect don't change, the drug concentration will not be changed.

2. Experiment Result

Compared with morphine, the compound I-6 does not produce significant tolerance phenomena in mice test. The result is shown in the following figure, morphine has attenuated analgesic effect from Day 2, and has no significant analgesic effect at dosage of 7 mg/kg on Day 3, and higher dosage is required to restore its analgesic effect. While the compound I-6 has no such phenomena. The result is shown in FIG. 1.

Experiment Embodiment 5: Physical Dependence Test after Chronic Administration of Compound I-6

1. Procedure

Kuming mice (18-20 g, male) are selected, and divided into physiological saline group, morphine group, and I-6 group.

Administration Method:

physiological saline group: subcutaneous injection, 0.2 mL for each mice, continuous administration for 10 days.

morphine group: subcutaneous injection, administration according to an escalating dose schedule, 20, 40, 60, 80, 100 mg/kg, continuous administration for 10 days, two injections per day at 8 hours interval, administration with escalating concentration, and 100 mg/kg is maintained from the fifth injection until Day 10.

I-6 group: subcutaneous injection, administration according to an escalating dose schedule, 50, 100, 150, 200, 300 µg/kg, continuous administration for 10 days, two injections per day at 8 hours interval, administration with escalating concentration, and 300 µg/kg is maintained from the fifth injection until Day 10.

2 hours after the end administration on the Day 10, each group is peritoneally administered with Naloxone 3 mg/kg, and jump times and weight reduction of mice within 20 min in each group are observed.

2. Experiment Result

Figure 2:
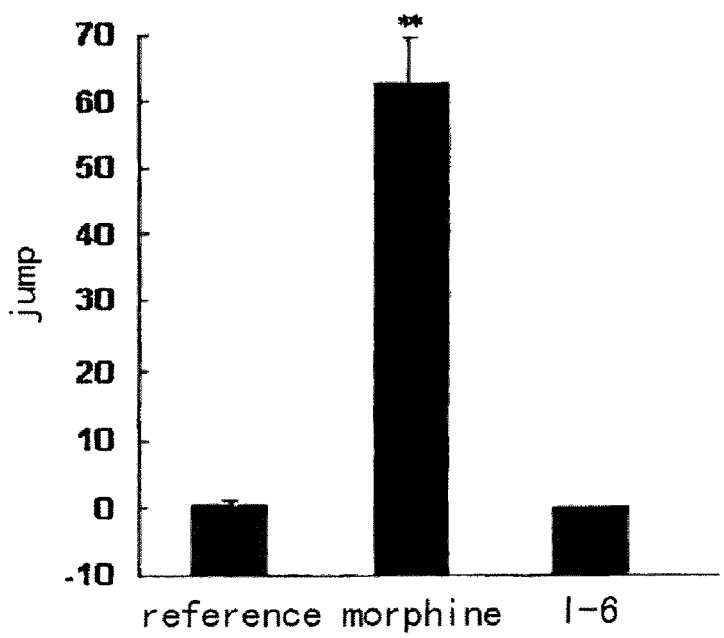
FIG. 2 is mice jumping conditions for Naloxone administration 3 mg/kg after the compound I6 is administered for 10 days. (**compared with reference group, p<0.01)
Figure 3:
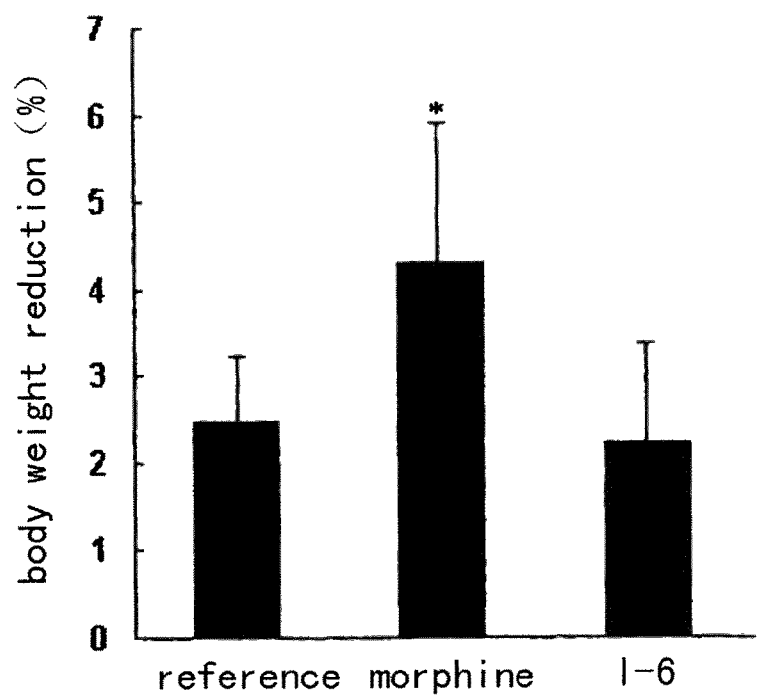
FIG. 3 is mice weight reduction conditions for Naloxone administration 3 mg/kg after the compound I6 is administered for 10 days. (**compared with reference group, p<0.05)

Compared with jump times and body weight reduction of mice caused by Naloxone-induced morphine physical dependence, the compound I-6 causes no physical dependence like morphine after continuous administration. As shown in FIG. 2 and FIG. 3, for the mice which are peritoneal administrated of Naloxone 3 mg/kg after continuous administration of I-6 for 10 days, their jump test result and body weight reduction are similar to those of physiological saline group.

Experiment Embodiment 6: Influence Test of Compound I-6 on Physical Dependence Caused By Morphine 1. Procedure:

Kuming mice (18-20 g, male) are selected and divided into physiological saline group, morphine group, and I-6+morphine group.

Administration Method:

physiological saline group: subcutaneous injection, 0.2 mL for each mouse, continuous administration for 10 days.

morphine group: subcutaneous injection, administration according to an escalating dose schedule, 20, 40, 60, 80, 100 mg/kg, continuous administration for 10 days, two injections per day at 8 hours interval, administration with escalating concentration, and 100 mg/kg is maintained from the fifth injection until Day 10.

I-6+morphine group: subcutaneous injection of morphine according to 20, 40, 60, 80, 100 mg/kg, continuous administration for 10 days, two injections per day at 8 hours interval, administration with escalating concentration, and 100 mg/kg is maintained from the fifth injection until Day 10; 300 µg/kg of compound I-6 is administered peritonally 10 min before administration of morphine every day.

2 hours after the end administration on Day 10, each group is peritoneally administered with Naloxone 3 mg/kg, and jump times and weight reduction of mice within 20 min in each group are observed.

Figure 4:
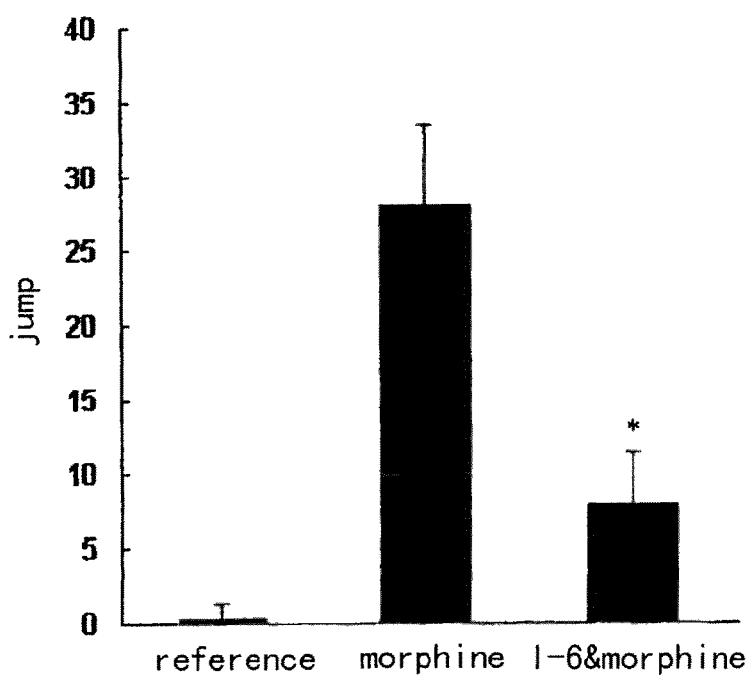
FIG. 4 is the effect of the compound I6 for resisting morphine addiction (*compared with morphine group, p<0.05)

2. Experiment Result:

The result shows that the compound I-6 can resist physical dependence caused by morphine. By using jump times of morphine physical dependence mice after Naloxone-induced as index, peritoneal administration of the compound I-6 300 µg/kg 10 min before administration of morphine every day can significantly reduce jump times of Naloxone-induced mice. The result is shown in FIG. 4.

The symbol of the compound in the pharmacological experiment is same as that of the compound in the embodiment.

The invention claimed is:

1. A compound of general formula (I) or its pharmaceutically acceptable salt:

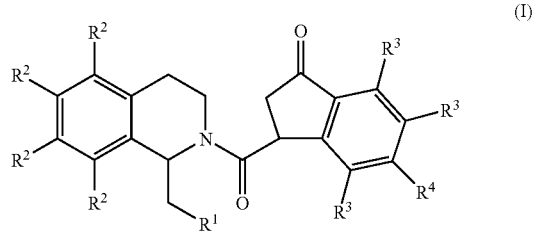
(I)

wherein $R^1$ is

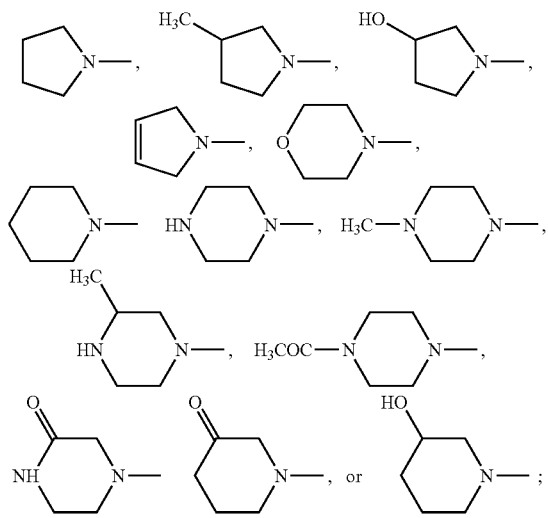

each $R^2$ independently is H, F, Cl, Br, $C_1$-$C_4$ alkyl, $OR^5$, or $NR^6R^7$, or all $R^2$s together with the benzene ring form 5,6-methylenedioxy, 6,7-methylenedioxy, or 7,8-methylenedioxy;

$R^3$ and $R^4$ each independently is H, F, Cl, Br, trifluoromethyl, $C_1$-$C_4$ alkyl, $OR^5$, or $NR^8R^9$, or all $R^2$s together with the benzene ring form 4,5-methylenedioxy, 5,6-methylenedioxy, or 6,7-methylenedioxy;

$R^5$ is H, $C_1$-$C_4$ alkyl, or allyl;

$R^6$ and $R^7$ each independently is H or $C_1$-$C_4$ alkyl; and $R^8$ and $R^9$ each independently is H, $C_1$-$C_4$ alkyl, or allyl.

2. The compound according to claim 1, wherein $R^1$ is

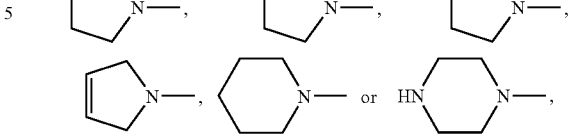

each $R^2$ independently is H, F, Cl, methyl, or methoxy, or all $R^2$s together with the benzene ring form 5,6-methylenedioxy or 6,7-methylenedioxy; and $R^3$ and $R^4$ each independently represent H, F, Cl, methyl, methoxy, dimethylamino, or all $R^3$s and $R^4$s together with the benzene ring form 4,5-methylenedioxy, 5,6-methylenedioxy or 6,7-methylenedioxy.

3. The compound according to claim 2, wherein $R^1$ represents

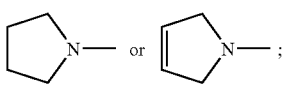

each $R^2$ independently is H, F, Cl or methoxy; and $R^3$ and $R^4$ each independently is H, F, Cl or methoxy.

4. The compound according to claim 3, wherein $R^1$ is

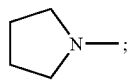

$R^2$ is H;

$R^3$ is H; and $R^4$ is Cl.

5. The compound according to claim 1, wherein the pharmaceutically acceptable salt is an acid addition salt formed by the compound of the general formula I and at least one of the following acids: hydrochloric acid, hydrobromic acid, sulfuric acid, carbonic acid, citric acid, tartaric acid, phosphoric acid, lactic acid, pyruvic acid, acetic acid, maleic acid, methylsulfonic acid, phenylsulfonic acid, p-toluenesulfonic acid, or arginine.

6. A method of preparing the compound of formula (I), comprising:

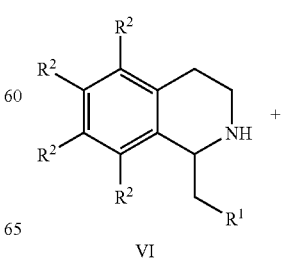
VI

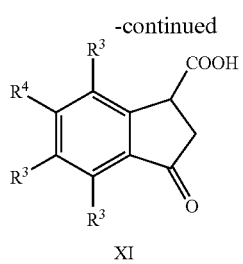

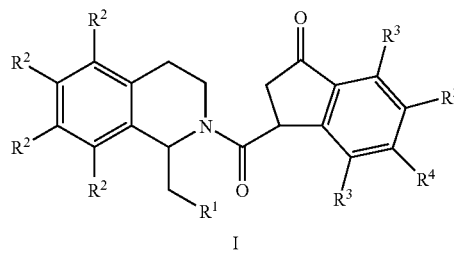

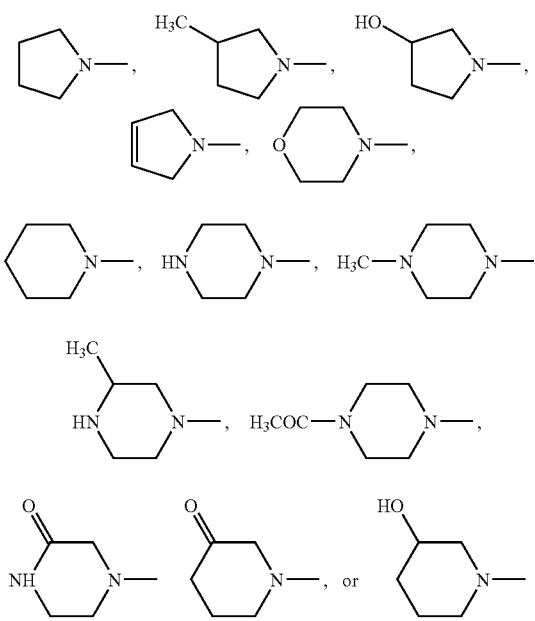

reacting a compound of formula (VI) and a compound of formula (XI) in the presence of a condensing agent selected from dicyclohexylcarbodiimide or 1-ethyl-3-(3-dimethylaminopropyl) carbodiimide hydrochloride) and a catalyst selected from 4-dimethylaminopyridine or 1-(hydroxybenzotriazole) in a solvent selected from dichloromethane, 1,2-dichloroethane, acetonitrile, N,N-dimethylformamide, N,N-dimethylacetamide, or dimethyl sulfoxide, to obtain the compound of general formula (I), wherein the $R^1$, $R^2$, $R^3$, and $R^4$ have the same definitions as those in claim 1.

7. A method for treating pain or morphine addiction withdrawal, comprising: administering the compound of claim 1 to a subject.

8. A pharmaceutical composition, containing an effective amount of a compound of general formula (I)

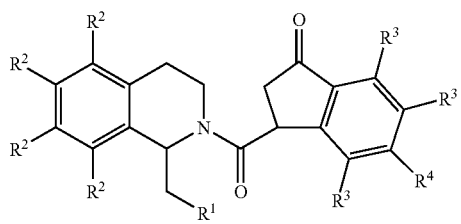

wherein $R^1$ represents:

each $R^2$ independently is H, F, Cl, Br, $C_1$-$C_4$ alkyl, $OR^5$, or $NR^6R^7$, or all $R^2$s together with the benzene ring form 5,6-methylenedioxy, 6,7-methylenedioxy, or 7,8-methylenedioxy;

$R^3$ and $R^4$ each independently is H, F, Cl, Br, trifluoromethyl, $C_1$-$C_4$ alkyl, $OR^5$, or $NR^8R^9$, or all $R^3$s and $R^4$s together with the benzene ring form 4,5-methylenedioxy, 5,6-methylenedioxy, or 6,7-methylenedioxy;

$R^5$ is H, $C_1$-$C_4$ alkyl, or allyl;

$R^6$ and $R^7$ each independently is H, $C_1$-$C_4$ or alkyl; and $R^8$ and $R^9$ each independently is H, $C_1$-$C_4$ alkyl, or allyl.

9. A method for treating pain or morphine addiction withdrawal, comprising administering the pharmaceutical composition of claim 8 to a subject.

10. A method of competitively inhibiting binding to the κ-opioid receptor comprising administering the pharmaceutical composition of claim 8 to a subject.

* * * * *